United States Patent
Okamoto et al.

(10) Patent No.: US 8,742,136 B2
(45) Date of Patent: Jun. 3, 2014

(54) METHOD FOR PRODUCING CYCLIC DISULFONIC ACID ESTER

(75) Inventors: Kuniaki Okamoto, Kawagoe (JP); Tsutomu Watahiki, Kawagoe (JP); Motoshige Sumino, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 996 days.

(21) Appl. No.: 12/304,409

(22) PCT Filed: Jun. 14, 2007

(86) PCT No.: PCT/JP2007/061998
§ 371 (c)(1), (2), (4) Date: Dec. 11, 2008

(87) PCT Pub. No.: WO2007/148597
PCT Pub. Date: Dec. 27, 2007

(65) Prior Publication Data
US 2009/0281333 A1    Nov. 12, 2009

(30) Foreign Application Priority Data
Jun. 19, 2006 (JP) ................................. 2006-168643

(51) Int. Cl.
*C07D 327/00* (2006.01)

(52) U.S. Cl.
CPC .................................... *C07D 327/00* (2013.01)
USPC ............................................. 549/19; 549/11

(58) Field of Classification Search
CPC ..................................................... C07D 327/00
USPC ....................................................... 549/11, 19
See application file for complete search history.

(56) References Cited

U.S. PATENT DOCUMENTS

| | | | |
|---|---|---|---|
| 3,970,671 A * | 7/1976 | Kondo et al. | 549/224 |
| 4,087,551 A * | 5/1978 | May | 514/659 |
| 4,613,676 A * | 9/1986 | Fuhrer et al. | 560/39 |
| 4,950,768 A | 8/1990 | Cronyn | |

FOREIGN PATENT DOCUMENTS

| | | |
|---|---|---|
| JP | 61-501089 A | 5/1986 |
| JP | 5-213854 A | 8/1993 |
| JP | 2005-336155 A | 12/2005 |
| JP | 2005-336255 A | 12/2005 |
| JP | 2006-188449 A | 7/2006 |

OTHER PUBLICATIONS

Takeuchi et al. Chemistry Letters 1980, 11, 1395-1398.*
Takeuchi et al. Tetrahedron 1987, 43, 701-709.*
Creary et al. J. Org. Chem. 2003, 68, 8683-8692.*
Winter et al. Journal of Fluorine Chemistry 2006, 127, 1188-1194.*
Frasch et al. Chem. Ber. 1992, 125, 1763-1767.*
CASREACT Record of Frasch et al. Chem. Ber. 1992, 125, 1763-1767.*
CASREACT Record of Larpent et al. Synthetic Communications 1991, 21, 495-503.*
International Search Report of PCT/JP2007/061998, dated Aug. 21, 2007.

* cited by examiner

*Primary Examiner* — Joseph Kosack
*Assistant Examiner* — Matthew Coughlin
(74) *Attorney, Agent, or Firm* — Hamre, Schumann, Mueller & Larson, P.C.

(57) ABSTRACT

It is an object of the present invention to provide a commercially advantageous method for producing a cyclic disulfonic acid ester with high yield, the present invention discloses a method for producing a cyclic disulfonic acid ester represented by the general formula (3), which comprises reacting a silver alkanedisulfonate represented by the general formula (1) with a dihaloalkane represented by the general formula (2) in a nonpolar solvent.

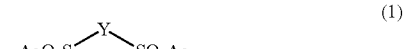

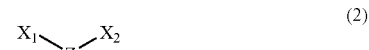

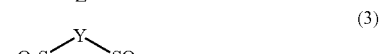

Wherein $X_1$ and $X_2$ are each independently a chlorine atom, a bromine atom or an iodine atom; and Y and Z are each independently a substituted or unsubstituted alkylene chain which may have a heteroatom in the chain.

3 Claims, No Drawings

METHOD FOR PRODUCING CYCLIC DISULFONIC ACID ESTER

TECHNICAL FIELD

The present invention relates to a method for producing a cyclic disulfonic acid ester.

BACKGROUND OF THE INVENTION

Cyclic disulfonic acid esters are expecting compounds as effective materials for treatment such as melanotic cancer, ovary cancer, as well as leukemia (see, e.g. JP-A-61-501089). As a method for producing these cyclic disulfonic acids, the following methods have been known: <1> a method of synthesizing said cyclic disulfonic acid ester by adding a dihaloalkane to a solution prepared by reacting a silver salt such as silver carbonate with an alkanedisulfonyl chloride dissolved in a suitable polar solvent such as acetonitrile (see, e.g. JP-A-61-501089); <2> a method of synthesizing said cyclic disulfonic acid ester by adding a tertiary amine and an alkanedisulfonyl chloride dissolved in a suitable solvent such as tetrahydrofuran to a diol such as ethylene glycol dissolved in the same solvent described above (see, e.g. JP-A-61-501089); <3> a method of synthesizing said cyclic disulfonic acid ester by reacting at least one kind of compound selected from the group consisting of an alkanedisulfonic acid anhydride, an alkanedisulfonic acid and a halogenated sulfonylalkanesulfonic acid with a diacyloxyalkane or a dialkylsulfonyloxyalkane (see, e.g. JP-A-2005-336155); and the like.

However, the method of the above <1> is not necessarily advantageous for commercial production because yield of the desired cyclic disulfonic acid ester is low. In the method of the above <2>, there are such problems that yield of the desired cyclic disulfonic acid ester is also low, and further that a cyclic disulfonic acid ester derived from a diol having one carbon atom, among cyclic disulfonic acid esters, cannot be synthesized by this method, because only a diol having 2 or more carbon atoms call be used. In addition, also in the method of the above <3>, there are such problems that yield of the desired cyclic disulfonic acid ester is low similarly to the methods of the above <1> and <2>, and further that since alkanedisulfonic acid, anhydride thereof and halogenated sulfonylalkanesulfonic acid as a starting material further requires carrying out anhydration of hydrate or dehydration condensation after reacting their corresponding alkanedisulfonyl halide with water, preparation of the starting material takes extra effort. Under such circumstance, development of a method for producing a cyclic disulfonic acid ester which can be applied to various cyclic disulfonic acid esters and gives high yield suitable for commercial production has been required.

DISCLOSURE OF INVENTION

Problem to be Solved by the Invention

The present invention provides a commercially advantageous method for producing a cyclic disulfonic acid ester with high yield.

Means to Solving the Problem

The present invention is a method for producing a cyclic disulfonic acid ester represented by the general formula (3), which comprises reacting a silver alkanedisulfonate represented by the general formula (1) with a dihaloalkane represented by the general formula (2) in a nonpolar solvent:

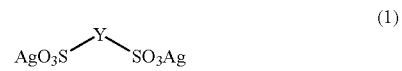

wherein Y is a substituted or unsubstituted alkylene chain which may have a heteroatom in the chain,

wherein $X_1$ and $X_2$ are each independently a chlorine atom, a bromine atom or an iodine atom; and Z is a substituted or unsubstituted alkylene chain which may have a heteroatom in the chain,

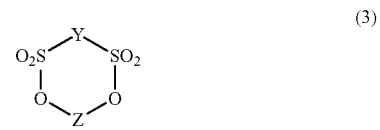

wherein Y and Z are the same to the above.

Effect of the Invention

According to the production method of the present invention, the desired cyclic disulfonic acid ester represented by the general formula (3) can be produced with high yield.

BEST MODE FOR CARRYING-OUT OF THE INVENTION

The "heteroatom" in the phrase "a substituted or unsubstituted alkylene chain which may have a heteroatom in the chain" represented by Y and Z in the general formulae (1), (2) and (3), specifically includes, for example, an oxygen atom, a sulfur atom, a nitrogen atom, and the like, and among others, an oxygen atom and a sulfur atom are preferable, and an oxygen atom is more preferable.

As $X_1$ and $X_2$ in the general formula (2), a bromine atom and an iodine atom are more preferable, and an iodine atom is further more preferable.

In the silver alkanedisulfonate represented by the above general formula (1) and the cyclodisulfonic acid ester represented by the above general formula (3), the substituted or unsubstituted alkylene chain which may have a heteroatom in the chain represented by Y includes an alkylene chain having generally 1 to 8 carbon atoms, preferably 1 to 4 carbon atoms, and more preferably one carbon atom, which is specifically exemplified by the general formula (4):

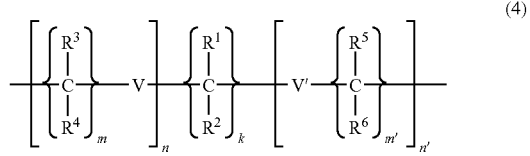

wherein k number of $R^1$ and $R^2$, m-by-n number of $R^3$ and $R^4$ and m'-by-n' number of $R^5$ and $R^6$ are each independently a hydrogen atom, a fluorine atom, an alkyl group, a perfluoroalkyl group, an aryl group or an aralkyl group; and n number of V and n' number of V' are each independently an oxygen atom, a sulfur atom or a group represented by the general formula (5):

(5)

wherein $R^7$ is an alkyl group, a perfluoroalkyl group, an aryl group or an aralkyl group; and k is an integer of 1 to 4; and m and m' are each independently an integer of 1 to 2; and n and n' are each independently an integer of 0 to 1. In this connection, the above number of carbon atom in the alkylene chain represented by Y means a number of carbon atom constructing a main chain, and does not include a number of carbon atom constructing a side chain.

In the dihaloalkane represented by the above general formula (2) and the cyclic disulfonic acid ester represented by the above general formula (3), the substituted or unsubstituted alkylene chain which may have a heteroatom represented by Z in the chain includes an alkylene chain having generally 1 to 8 carbon atoms, preferably 1 to 4 carbon atoms, and more preferably one carbon atom, which is specifically exemplified by the general formula (6):

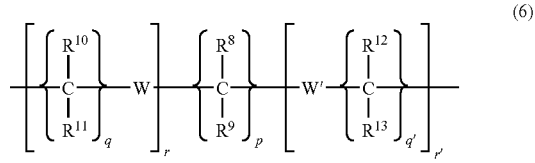

(6)

wherein p number of $R^8$ and $R^9$, q-by-r number of $R^{10}$ and $R^{11}$ and q'-by-r' number of $R^{12}$ and $R^{13}$ are each independently a hydrogen atom, a fluorine atom, an alkyl group, a perfluoroalkyl group, an aryl group or an aralkyl group; and r number of W and r' number of W' are each independently an oxygen atom, a sulfur atom or a group represented by the general formula (7):

(7)

wherein $R^{14}$ is an alkyl group, a perfluoroalkyl group, an aryl group or an aralkyl group; and p is an integer of 1 to 4; and q and q' are each independently an integer of 1 to 2; and r and r' are each independently an integer of 0 to 1. In this connection, the above number of carbon atom in the alkylene chain represented by Y means a number of carbon atom constructing a main chain, and does not include a number of carbon atom constructing a side chain.

The alkyl group represented by $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ in the general formulae (4), (5), (6) and (7) may be any one of straight-chained, branched or cyclic group, and includes one having generally 1 to 6 carbon atoms, and preferably 1 to 2 carbon atoms, which is specifically exemplified by, for example, a methyl group, an ethyl group, a n-propyl group, an isopropyl group, a cyclopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1-ethylpropyl group, a cyclopentyl group, a n-hexyl group, an iso-hexyl group, a sec-hexyl group, a tert-hexyl group, a neohexyl group, a 2-methylpentyl group, a 1,2-dimethylbutyl group, a 1-ethylbutyl group, a cyclohexyl group, and the like, and among others, a methyl group and an ethyl group are preferable.

The perfluoroalkyl group represented by $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ in the general formulae (4), (5), (6) and (7) may be any one of straight-chained, branched or cyclic group, and includes one having generally 1 to 6 carbon atoms, and preferably 1 to 2 carbon atoms, which is specifically exemplified by, for example, a perfluoromethyl group, a perfluoroethyl group, a perfluoro-n-propyl group, a perfluoroisopropyl group, a perfluorocyclopropyl group, a perfluoro-n-butyl group, a perfluoroisobutyl group, a perfluoro-sec-butyl group, a perfluoro-tert-butyl group, a perfluorocyclobutyl group, a perfluoro-n-pentyl group, a perfluoroisopentyl group, a perfluoro-sec-pentyl group, a perfluoro-tert-pentyl group, a perfluoroneopentyl group, a perfluoro-2-methylbutyl group, a perfluoro-1-ethylpropyl group, a perfluorocyclopentyl group, a perfluoro-n-hexyl group, a perfluoroisohexyl group, a perfluoro-sec-hexyl group, a perfluoro-tert-hexyl group, a perfluoroneohexyl group, a perfluoro-2-methylpentyl group, a perfluoro-1,2-dimethylbutyl group, a perfluoro-1-ethylbutyl group, a perfluorocyclohexyl group, and the like, and among others, a perfluoromethyl group and a perfluoroethyl group are preferable.

The aryl group represented by $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ in the general formulae (4), (5), (6) and (7) includes one having generally 6 to 14 carbon atoms, and preferably 6 carbon atoms, which is specifically exemplified by, for example, a phenyl group, a naphthyl group, an anthryl group, a phenanthryl group, and the like, and among others, phenyl group is preferable.

The aralkyl group represented by $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ in the general formulae (4), (5), (6) and (7) includes one having generally 7 to 15 carbon atoms, and preferably 7 carbon atoms, which is specifically exemplified by, for example, a benzyl group, a phenethyl group, an α-methylbenzyl group, a 1-methyl-1-phenylethyl group, a phenylpropyl group, a phenylbutyl group, a phenylpentyl group, a 1,2,3,4-tetrahydronaphthyl group, a naphthylmethyl group, a naphthylethyl group, a fluorenylmethyl group, an anthrylmethyl group, a phenanthrylmethyl group, and the like, and among others, benzyl group is preferable.

As $R^1$, $R^2$, $R^3$, $R^4$, $R^5$, $R^6$, $R^8$, $R^9$, $R^{10}$, $R^{11}$, $R^{12}$ and $R^{13}$ in the general formulae (4) and (6), a hydrogen atom and a fluorine atom are more preferable, and a hydrogen atom is further more preferable.

As $R^7$ and $R^{14}$ in the general formulae (5) and (7), an alkyl group and a perfluoroalkyl group are more preferable, and an alkyl group is further more preferable.

As V, V', W and W' in the general formulae (4) and (6), an oxygen atom and a sulfur atom are more preferable, and an oxygen atom is further more preferable.

k and p in the general formulae (4) and (6) are generally an integer of 1 to 4, preferably an integer of 1 to 2, and more preferably 1.

m, m', q and q' in the general formulae (4) and (6) are generally an integer of 1 to 2, and preferably 1.

n, n', r and r' in the general formulae (4) and (6) are generally an integer of 0 to 1, and preferably 0.

In the silver alkanedisulfonate represented by the above general formula (1), among the substituted or unsubstituted alkylene chain which may have a heteroatom represented by Y in the chain, the one which does not have a heteroatom in the chain is preferable, and specifically the substituted or unsubstituted alkylene chain in which Y in the above general formula (1) is represented by the general formula (8):

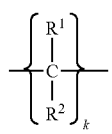
(8)

wherein $R^1$, $R^2$ and k are the same to the above, is preferable. In this connection, the alkylene chain represented by the general formula (8) corresponds to the case when n and n' in the above general formula (4) are 0. A cyclic disulfonic acid ester synthesized by reacting such silver alkanedisulfonate with the dihaloalkane represented by the above general formula (2) is specifically exemplified by, for example, the ester represented by the general formula (10):

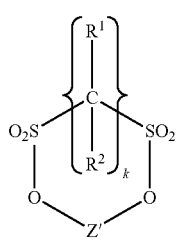
(10)

wherein Z' is the substituted or unsubstituted alkylene chain which may have a heteroatom in the chain represented by the above general formula (6) and $R^1$, $R^2$ and k are the same to the above. That is, the present invention is a preferable production method as a method for synthesizing a cyclic disulfonic acid ester represented by the above general formula (10).

Further, in a combination of the case when Y in the above general formula (1) is represented by the above general formula (8), and the case when the substituted or unsubstituted allylene chain which may have a heteroatom in the chain represented by Z in the dihaloalkane represented by the above general formula (2), Z is the one which does not have a heteroatom in the chain is more preferable, and specifically the combination of the case when Y in the above general formula (1) is the substituted or unsubstituted alkylene chain represented by the above general formula (8), and the case when Z in the above general formula (2) is the substituted or unsubstituted alkylene chain represented by the general formula (9):

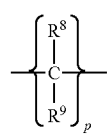
(9)

wherein $R^8$, $R^9$ and p are the same to the above, is more preferable. In this connection, the alkylene chain represented by the general formula (9) corresponds to the case when r and r' in the above general formula (6) are 0. A cyclic disulfonic acid ester synthesized by reacting such silver alkanedisulfonate with dihaloalkane is specifically exemplified by the general formula (11):

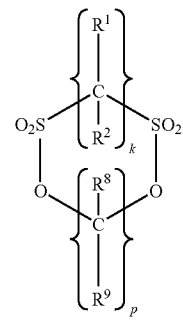
(11)

wherein $R^1$, $R^2$, $R^8$, $R^9$, k and p are the same to the above. That is, the present invention is a more preferable production method as a method for synthesizing a cyclic disulfonic acid ester represented by the above general formula (11).

Furthermore, the present invention is particularly useful as a production method for synthesizing a cyclic disulfonic acid ester having 2 carbon atoms by reacting a silver alkanedisulfonate having one carbon atom with a dihaloalkane having one carbon atom. Specifically, the case when the silver alkanedisulfonate represented by the above general formula (1) is silver methanedisulfonate represented by the formula (12):

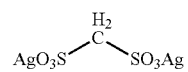
(12)

and the dihaloalkane represented by the above general formula (2) is diiodomethane represented by the formula (13):

(13)

and the cyclic disulfonic acid ester represented by the above general formula (3) is methylene methanedisulfonate represented by the formula (14):

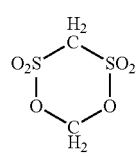
(14)

is particularly preferable. That is, the present invention is a particularly preferable production method as a method for synthesizing a cyclic disulfonic acid ester represented by the above formula (14).

As the silver alkanedisulfonate to be used in the present invention, the one which is synthesized by the method described, for example, in JP-A-5-213854 and the like may be arbitrarily used. Specifically, for example, the silver alkanedisulfonate can be synthesized by adding a silver salt such as silver carbonate to a solution prepared by dissolving an alkane disulfonic acid in a suitable solvent such as acetonitrile in advance to react them, and removing unreacted silver salt such as silver carbonate by filtering off this reaction mixture, and purifying by recrystallizing from a suitable solvent. In addition, for example, a silver alkanedisulfonate, in which Y in the above general formula (1) is a substituted or unsubstituted alkylene chain having a heteroatom in the chain, can be obtained firstly by synthesizing an alkanedisulfonic acid by a common synthesis method for ether, sulfide or tertiary amine, such as a synthesis method by reacting, for example, hydroxyalkylsulfonic acid, mercaptoalkylsulfonic acid, aminoalkylsulfonic acid or the like with a haloalkylsulfonic acid and then reacting thereto a silver salt such as silver carbonate in the same manner as above.

As the dihaloalkane to be used in the present invention, commercially available one or synthesized one by a common method may be arbitrarily used. Specifically, for example, the dihaloalkane, in which Z in the above general formula (2) is a substituted or unsubstituted alkylene chain having a heteroatom in the chain, can be obtained by a common synthesis method for ether, sulfide or tertiary amine, such as a synthesis method by reacting, for example, diol, dithiol or the like, or monoamine, diamine or the like with a dihaloalkane which does not have a heteroatom in the chain.

In the production method of the present invention, a cyclic disulfonic acid ester represented by the general formula (3) can be synthesized by reacting a silver alkanedisulfonate represented by the general formula (1) with a dihaloalkane represented by the general formula (2) of a prescribed amount to the silver alkanedisulfonate in the presence of a catalyst if necessary, in a nonpolar solvent and then isolating and purifying from the reaction mixture by a common method. Specific isolation and purification method includes, for example, a method in which reaction mixture is filtered to remove precipitates (insoluble matter), and impurities are adsorbed using activated charcoal, then recrystallization is carried out from a suitable solvent, and the like.

An amount of the dihaloalkane represented by the general formula (2) to be used is generally 0.8 to 10 equivalents, and preferably 0.8 to 2 equivalents, relative to the silver alkanedisulfonate represented by the general formula (1). When the amount is less than 0.8 equivalent, yield of the desired cyclic disulfonic acid ester decreases. On the other hand, though an amount over 10 equivalents of the dihaloalkane can be used, such problems occur, for example, that yield of the desired cyclic disulfonic acid ester represented by the general formula (3) decreases because 2 moles of the dihaloalkane reacts to 1 mole of silver alkanedisulfonate, and that economical efficiency becomes impaired.

Reaction temperature may be set a temperature at which a silver alkanedisulfonate represented by the general formula (1) and a dihaloalkane represented by the general formula (2) react, and the temperature is preferably set a temperature at which a silver alkanedisulfonate and a dihaloalkane react effectively, and a cyclic disulfonic acid ester can be synthesized with high yield. Specifically, temperature is generally 0 to 200° C., preferably 50 to 150° C., and more preferably 70 to 130° C. At a temperature lower than 0° C., the reaction hardly proceeds, and yield of the desired cyclic disulfonic acid ester significantly decreases. In contrast, at a temperature over 200° C., such problems occur that the reaction product could lead to be decomposed, and the like.

In the production method of the present invention, a catalyst may be used so that reaction proceeds smoothly. The catalyst includes oxide of metal or semimetal, solid acid, metal- or semimetal-based halogenide salt, inorganic acid salt, organic acid salt or these salts supported by a carrier such as polymeric compound and ion-exchange resin. The oxide of metal or semimetal includes, for example, titanium dioxide, zirconium dioxide, magnesium oxide, aluminum oxide, silicon dioxide and the like. The solid acid includes, for example, zeolite, kaolinite, montmorillonite and the like. The metal or the semimetal of metal- or semimetal-based halogenide salt, inorganic acid salt, organic acid salt or these salts supported by a carrier such as polymeric compound and the like includes, for example, boron, aluminum, scandium, titanium, vanadium, chromium, manganese, iron, cobalt, nickel, copper, zinc, zirconium, niobium, ruthenium, rhodium, palladium, silver, stannum, cerium, samarium, ytterbium, tantalum, iridium, platinum, gold, lead, and the like. The halogenide of the metal- or semimetal-based halogenide salt includes, for example, fluoride, chloride, bromide, iodide, and the like. The inorganic acid of the metal- or semimetal-based inorganic acid salt includes hydroxyl compound, sulfuric acid, nitric acid, phosphoric acid, and the like. The organic acid of the metal- or semimetal-based organic acid salt includes sulfonic acid, perhalogenosulfonic acid, carboxylic acid, carbonic acid, and the like. These salts are compounds made by combining the above metal or semimetal and halogenide, inorganic acid or organic acid. As the polymeric compound supporting these salts, any polymeric compound can be used, so long as it is commonly used in this field and can act as a carrier. As the ion-exchange resin, any type can be used so long as it is a cationic ion-exchange resin which is commonly used in this field. In addition, among these catalysts, the metal- or semimetal-based halogenide salt, inorganic acid salt, organic acid salt or these salts supported by a carrier such as polymeric compound are preferable, and the metal- or semimetal-based organic acid salt having Lewis acid property is more preferable. Specifically, these salts include, for example, copper trifluoromethanesulfonate and silver trifluoromethanesulfonate. These catalysts may be used alone or in a suitable combination of two or more kinds thereof. Though an amount of the catalyst to be used is not especially limited, for example, generally 0.001 to 0.5 equivalents, and preferably 0.02 to 0.2 equivalent, relative to the silver alkanedisulfonate represented by the general formula (1).

The nonpolar solvent to be used as a reaction solvent includes, for example, an aromatic hydrocarbon-based solvent such as benzene, toluene, o-xylene, m-xylene, p-xylene and the like, an aliphatic hydrocarbon-based solvent such as n-hexane, cyclohexane, n-heptane, cycloheptane, n-octane, isooctane, cyclooctane and the like, a carbonate ester type solvent such as dimethyl carbonate, diethyl carbonate and the like, an aromatic and/or aliphatic hydrocarbon-based solvent such as petroleum benzine, ligroin and the like, and a mixture of these solvents. Among others, an aliphatic hydrocarbon-based solvent such as n-hexane, cyclohexane, n-heptane, cycloheptane, n-octane, isooctane and cyclooctane is preferable, and cyclohexane, n-heptane, n-octane and isooctane are more preferable. Though an amount of these solvents to be used is not especially limited, for example, generally 0.5 to 5 L, and preferably 0.5 to 2 L per 1 mole of silver alkanedisulfonate represented by the general formula (1). In this connection, the reaction solvent in the production method of the present invention is a nonpolar solvent, and it has been found out first in the world by the present inventors that the cyclic disulfonic acid ester can be synthesized with high yield by using such solvent.

In the production method of the present invention, though the reaction can proceeds under any pressure condition of ordinary pressurized or reduced, the ordinary or pressurized condition is more preferable because reaction temperature can be set at the boiling point of the solvent or higher. In this connection, a method for synthesizing a cyclic disulfonic acid ester under the pressurized condition may be performed by conducting the reaction using an apparatus such as sealed tube, autoclave.

Reaction time can not be categorically determined because it may depend on equivalent amount of dihaloalkane relative to silver alkanedisulfonate, reaction temperature, kinds of reaction solvent, concentration of reaction solution, presence or absence of catalyst, an amount of catalyst to be used, and the like, but it is set in a range of generally 0.5 to 20 hours, and preferably 2 to 12 hours.

Hereinafter, the present invention will be specifically explained referring to Examples and Comparative Examples, but the present invention is not limited thereto by any means.

EXAMPLES

Example 1

Synthesis of Methylene Methanedisulfonate Using Isooctane as a Reaction Solvent

To a silver methanedisulfonate (20.0 g, 51.3 mmol) in isooctane (50 mL), diiodomethane (13.7 g, 51.3 mmol) was added dropwise, and the mixture was reacted at reflux for 4 hours. The reaction mixture was then cooled, and the desired product was extracted with adding ethyl acetate. The extract was concentrated under reduced pressure, to give crude product of methylene methanedisulfonate. After the crude product was dissolved in ethyl acetate, the solution was treated with activated charcoal, then concentrated. n-Hexane was added thereto, and precipitation was filtered, to obtain the precipitation and dried under reduced pressure to give methylene methanedisulfonate (7.8 g, yield: 81%) as white crystal. $^1$H-NMR (CD$_3$CN) δ: 5.30 (s, 2H), 5.97 (s, 2H); $^{13}$CNMR (CD$_3$CN) δ: 68.9, 91.8; Melting Point: 146° C.

Example 2

Synthesis of Methylene Methanedisulfonate Using Cyclohexane as a Reaction Solvent To a silver methanedisulfonate (2.0 g, 5.1 mmol) in cyclohexane (5 mL), diiodomethane (1.4 g, 5.1 mmol) was added dropwise, and the mixture was reacted at reflux for 4 hours. The reaction mixture was then cooled, and the desired product was extracted with adding ethyl acetate. The extract was concentrated under reduced pressure, to give crude product of methylene methanedisulfonate. Determination by internal reference method using $^1$H-NMR gave a reaction rate of 47%.

Example 3

Synthesis of Methylene Ethanedisulfonate Using n-Octane as a Reaction Solvent

To a silver ethanedisulfonate (5.0 g, 12 mmol) in n-octane (12 mL), diiodomethane (3.5 g, 13 mmol) was added dropwise, and the mixture was reacted at reflux for 4 hours. The reaction mixture was then cooled, and the desired product was extracted with adding acetone. The extract was concentrated under reduced pressure, to give crude product of methylene ethanedisulfonate. Determination by internal reference method using $^1$H-NMR gave reaction rate of 51%. $^1$H-NMR (CD$_3$CN) δ: 3.80 (s, 4H), 5.59 (s, 2H); $^{13}$C-NMR (CD$_3$CN) δ: 46.8, 89.8.

Example 4

Synthesis of Methylene Methanedisulfonate Using Cyclohexane as a Reaction Solvent Under a Pressurized Condition After silver methanedisulfonate (2.0 g, 5.1 mmol) and cyclohexane (5 mL) were charged into a sealed tube, diiodomethane (1.4 g, 5.1 mmol) was added dropwise to the mixture, and the sealed tube was hermetically sealed. The reaction mixture was heated to 120° C., and reacted with stirring for 4 hours. The reaction mixture was then cooled, and the desired product was extracted with adding ethyl acetate. The extract was concentrated under reduced pressure, to give crude product of methylene methanedisulfonate. Determination by internal reference method using $^1$H-NMR gave a reaction rate of 89%.

Comparative Example 1

Synthesis of Methylene Methanedisulfonate Using Acetonitrile as a Reaction Solvent To a silver methanedisulfonate (2.0 g, 5.1 mmol) in acetonitrile (5 mL), diiodomethane (1.4 g, 5.1 mmol) was added dropwise, and the mixture was reacted at reflux for 4 hours. The reaction mixture was then cooled, and the desired product was extracted with adding ethyl acetate. The extract was concentrated under reduced pressure, to give crude product of methylene methanedisulfonate. Determination by internal reference method using $^1$H-NMR gave a reaction rate of 15%.

From the results of Examples 1 to 4 and Comparative Example 1, it is understood that a cyclic disulfonic acid ester can be given in high yield by reacting in a nonpolar solvent. Further, it is also understood that a cyclic disulfonic acid ester can be given in higher yield by reacting at a prescribed temperature using a sealed tube or the like.

INDUSTRIAL APPLICABILITY

The production method of the present invention enables commercial production and the like of cyclic disulfonic acid esters which are expected as effective materials for treatment such as, for example, leukemia, melanotic cancer, ovary cancer.

What is claimed is:

1. A method for producing a cyclic disulfonic acid ester, which comprises:
reacting a silver alkanedisulfonate represented by following formula (1) with a dihaloalkane represented by following formula (2) in a solvent selected from the group consisting of cyclohexane, n-octane, isooctane, and a mixture of two or three solvents thereof:

(1)

wherein Y is represented by following formula (8):

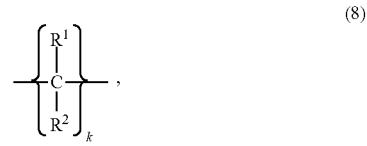

(8)

wherein k is an integer from 1 to 4, and R$^1$ and R$^2$ in each of the 1-4 k units are each independently hydrogen, fluorine, an alkyl group, a perfluoroalkyl group, an aryl group, or an aralkyl group, and;

(2)

wherein $X_1$ and $X_2$ are each independently chlorine, bromine, or iodine, and Z is represented by following formula (9):

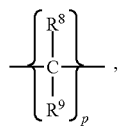
(9)

wherein p is an integer from 1 to 4, and $R^8$ and $R^9$ in each of the 1-4 p units are each independently hydrogen, fluorine, an alkyl group, a perfluoroalkyl group, an aryl group, or an aralkyl group; and the cyclic disulfonic acid ester is represented by following formula (3):

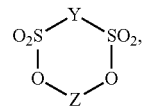
(3)

wherein Y and Z are same as described above.

2. The method according to claim 1, wherein the silver alkanedisulfonate represented by the formula (1) is silver methanedisulfonate, the dihaloalkane represented by the formula (2) is diiodomethane, and the cyclic disulfonic acid ester represented by the formula (3) is methylene methanedisulfonate.

3. The method according to claim 1, wherein reaction temperature is in a range from 50 to 150° C.

* * * * *